(12) United States Patent
Jackson et al.

(10) Patent No.: US 10,646,876 B2
(45) Date of Patent: May 12, 2020

(54) BIOCHIP STORAGE WELLS

(71) Applicant: Randox Laboratories Ltd., Northern Ireland (GB)

(72) Inventors: Stuart Jackson, Northern Ireland (GB); Ivan McConnell, Northern Ireland (GB); John Lamont, Northern Ireland (GB); Peter Fitzgerald, Northern Ireland (GB); Marc Wharry, Northern Ireland (GB)

(73) Assignee: RANDOX LABORATORIES LTD., Crumlin (GB)

( * ) Notice: Subject to any disclaimer, the term of this patent is extended or adjusted under 35 U.S.C. 154(b) by 387 days.

(21) Appl. No.: 15/534,460

(22) PCT Filed: Dec. 14, 2015

(86) PCT No.: PCT/GB2015/053983
§ 371 (c)(1),
(2) Date: Jun. 8, 2017

(87) PCT Pub. No.: WO2016/097711
PCT Pub. Date: Jun. 23, 2016

(65) Prior Publication Data
US 2017/0348692 A1      Dec. 7, 2017

(30) Foreign Application Priority Data
Dec. 15, 2014 (GB) .................. 1422231.9

(51) Int. Cl.
*B01L 9/00* (2006.01)
*C12M 1/00* (2006.01)
(Continued)

(52) U.S. Cl.
CPC ............... *B01L 9/52* (2013.01); *B01L 3/508* (2013.01); *B65B 7/2871* (2013.01); *C12M 23/38* (2013.01);
(Continued)

(58) Field of Classification Search
CPC ....... B01L 2200/142; B01L 2200/0689; B01L 9/52; B01L 7/2871
(Continued)

(56) References Cited

U.S. PATENT DOCUMENTS 2,958,439 A    11/1960   Yochem
4,084,718 A     4/1978   Wadsworth
(Continued)

FOREIGN PATENT DOCUMENTS

EP    0988893  A1        3/2000
EP    1864716  A1  *    12/2007  .......... B01L 3/50853
(Continued)

OTHER PUBLICATIONS

Jeberfeld, Jom, International Search Report, European Patent Office, PCT/GB2015/053983, dated Feb. 24, 2016.
(Continued)

*Primary Examiner* — King M Chu
(74) *Attorney, Agent, or Firm* — Gavrilovich, Dodd & Lindsey LLP (57) ABSTRACT

The present invention is directed to a cap for a biochip storage well. The cap comprises a resilient sealant layer capable, under the application of pressure, of forming a vapour-proof seal with a line contact interface formation extending around the perimeter of a biochip storage well. An assay assembly comprising the cap of the invention and a biochip storage is disclosed. Methods of sealing a biochip storage well using a cap of the invention are also disclosed.

16 Claims, 6 Drawing Sheets

(51) Int. Cl.
*B01L 3/00* (2006.01)
*B65B 7/28* (2006.01)

(52) U.S. Cl.
CPC . *B01L 2200/0689* (2013.01); *B01L 2200/142* (2013.01); *B01L 2300/042* (2013.01); *B01L 2300/044* (2013.01); *B01L 2300/045* (2013.01); *B01L 2300/047* (2013.01); *B01L 2300/0636* (2013.01); *B01L 2300/0832* (2013.01); *B01L 2300/161* (2013.01)

(58) Field of Classification Search
USPC .......................................................... 220/212
See application file for complete search history.

(56) References Cited

U.S. PATENT DOCUMENTS

| | | | |
|---|---|---|---|
| 5,720,406 A | 2/1998 | Fassbind et al. | |
| 7,247,497 B2* | 7/2007 | Dahm | B01L 3/5025 422/560 |
| 8,568,373 B2* | 10/2013 | Kuniyasu | A61M 25/002 206/303 |
| 2004/0258563 A1 | 12/2004 | Young et al. | |
| 2012/0329143 A1 | 12/2012 | Yamazaki et al. | |
| 2013/0309147 A1* | 11/2013 | Yu | B01L 3/50825 422/550 |
| 2014/0295578 A1 | 10/2014 | Tan et al. | |

FOREIGN PATENT DOCUMENTS

| | | |
|---|---|---|
| EP | 1864716 A1 | 12/2007 |
| WO | 2015/035953 A1 | 3/2015 |

OTHER PUBLICATIONS

Jeberfeld, Jom, Written Opinion of the International Search Authority European Patent Office, PCT/GB2015/053983, dated Jun. 23, 2016.

* cited by examiner

BIOCHIP STORAGE WELLS

CROSS REFERENCE TO RELATED APPLICATIONS

This application is a U.S. National Stage Application filed under 35 U.S.C. § 371 and claims the benefit of International Application No. PCT/GB2015/053983, filed Dec. 14, 2015, which application claims priority to Great Britain Application No. 1422231.9, filed Dec. 15, 2014, the disclosure of which are incorporated herein by reference.

FILED OF THE INVENTION

The invention is directed to improvements relating to biochip storage wells, specifically in the field of assay devices and assemblies.

BACKGROUND OF THE INVENTION

Assay devices in the form of biochips are well known in the field of immunoassays. Such biochips are often placed in storage wells and are deposited with an array of localised reactive sites containing potentially many different reactive species, for example, different proteins. These reactive species react with a respective different analyte in a sample supplied to the chip. Following removal of the unbonded sample, the biochip can then be examined to determine the presence or absence of the respective analytes.

An example of an assay assembly comprising a storage well and biochip is described in more detail in EP 0988893 A1. This application is incorporated herein by reference. The use of a storage well protects the assay device (in this case, the biochip) while it is being handled during an immunoassay process, and helps to prevent reactions sites from being damaged.

A problem with the assay assemblies described in the prior art is that the storage well should be sealed in order to reduce vapour loss during the heating stage of the immunoassay. When the well is heated during the run of an assay, depending on the temperature, there is the risk of fluid loss via vapour through the opening of the well cavity and the subsequent contamination of the environment, lab equipment or a biochip analyser. The assay could also be affected as the fluid loss through vapour would change the volumes of fluid in the biochip well. If the vapour loss were to be corrected for by adding additional fluid, this would incur an additional cost, and there would still be risk of contamination of the environment. Traditionally, the reduction of vapour loss is achieved by one of three means.

Firstly, oil is often used to form a seal on top of the fluid during heating. However, the scientist would be constrained to use only fluids of certain densities in assays, and would have to follow material disposal guidelines for oils. The oil would also coat the surface of the biochip if the fluid were removed from the well as part of the assay, or reduce sensitivity of detection by forming a layer between the camera and the biochip.

Alternatively, an adhesion film or foil is used to seal the assay during heating. This is suitable for manual assays, but the foil needs to be completely removed for imaging. Further, applying the foil as part of an automated process is a complicated, costly and space consuming task for a biochip analyser to perform and so is undesirable.

Finally, it is known in the art to use caps which are screw or plug based to seal the storage well during the run of an assay. However, such caps require complicated robotics to form a seal. Further, the thread in a screw cap is not vapour proof, resulting in some evaporation and loss of fluid through the thread at high temperatures or during prolonged time periods. Additionally, plug caps have an inherent risk of aggressive depression at high liquid temperatures, causing a sudden jerking motion which can result in droplets of fluid escaping. Therefore, both screw caps and plug caps harbour risks of contamination where hazardous fluids are present.

SUMMARY OF THE INVENTION

According to a first aspect, the present invention is an assay assembly comprising a biochip storage well having a base and one or more side walls, adapted to receive a biochip, with a line contact interface extending around the perimeter thereof and a cap according to the first aspect of the invention, wherein a vapour-proof seal can be formed between the resilient sealant layer of the cap and the line contact interface of the biochip storage well, when the resilient layer of the cap is applied under pressure against the line contact interface.

According to a second aspect, the present invention is a method of sealing a biochip storage well having a line contact interface surrounding the perimeter thereof, with a cap according to the first aspect of the invention having a resilient sealant layer, comprising the steps of;

placing the cap onto the biochip storage well so that the resilient sealant layer is above the line contact interface;

applying external force onto the cap so that the resilient sealant layer is pressed into the line contact interface, forming a vapour-proof seal.

In the present invention, a cap is provided to be used in conjunction with a receptacle such as an assay assembly comprising a biochip storage well and biochip. The invention overcomes the problems mentioned above by forming a tight vapour-proof seal between the resilient sealant layer and the biochip storage well. The cap provides a solution that is clean, disposable and does not contaminate the assay or reduce sensitivity of assays. Further, the cap uses a line contact interface principle resulting in a simple process for sealing (pressure is applied to form the seal, then stopped to release), which does not require complicated robotics. The line contact interface may be defined by a sharp edge such as a knife-edge which extends around the perimeter of the top face of the biochip storage well.

The cap may comprise a flat section above a resilient sealant layer. The resilient sealant layer is capable of forming a vapour-proof seal with the line contact interface of a biochip storage well. In a preferred embodiment, the flat section allows for the uniform application of force around the periphery of the cap, directly above the interface with the biochip storage well. This ensures a very tight vapour-proof seal between the biochip storage well and the resilient layer of the cap.

Preferably the biochip storage well is to be used with an assay device for immunoassays. Preferably the assay device is a biochip. In a preferred embodiment, the biochip storage well has a cavity fit to accommodate a 9×9×0.6 mm ceramic square biochip, with raised walls so that the biochip can be exposed to different fluids at different times during the run of an assay. The cavity opening is preferably large enough to accommodate machines to pick up and place biochips in the storage well.

In a preferred embodiment the cap stops fluid loss through evaporation during long incubation steps in an assay by forming a tight vapour-proof seal between the resilient sealant layer of the cap and the line contact interface of the biochip storage well.

In a preferred embodiment, the resilient sealant layer is a polymer sealant which is soft, chemically resistant and non-porous. This allows the resilient layer to flex under the application of pressure. Further, this means that the resilient layer does not react with any compounds used during an assay, and does not absorb any liquid. Preferably the sealant layer is a nitrile layer, such as a nitrile rubber layer. More preferably the nitrile layer is 0.1 mm to 10 mm in thickness, most preferably 1 mm in thickness. Preferably, the nitrile layer comprises Nitrile BS2751-BA60, produced by Martin's Rubber Company Limited. When force is applied to the cap, the resilient sealant layer presses into the line contact interface of the receptacle, forming a vapour-proof seal. The resilient sealant layer may also be polytetrafluoroethylene (PTFE) or a thermoplastic such as polychlorotrifluoroethylene (PCTFE) or polyethylene (PE). The thermal properties of the resilient sealant layer allow for the sealed biochip storage well to be heated to high temperatures, without degradation of the sealant layer. Further, the contact angle with aqueous fluid is high, therefore condensed vapour is likely to form droplets and fall in to the cavity of the biochip storage well.

In a preferred embodiment, the resilient sealant layer can be easily modified to improve its resistance to wetting (hydrophobicity). A thin hydrophobic layer can be coated on to the material, meaning that any vapour that does condense on the surface of the sealant layer does not react, is not contaminated and will form droplets which drop into the main cavity of the biochip storage well. By stopping evaporation, the cap also eliminates risk of contamination of the environment, lab apparatus and biochip analysers.

In a preferred embodiment, the vapour-proof seal between the resilient layer of the cap and the line contact interface of the biochip storage well requires pressure from an external force of 2 N or more, preferably 10-50 N. In a preferred embodiment, this allows a tight seal to form, which means more labile and corrosive fluids can be used in assays without risk of contamination or fluid loss. In a preferred embodiment, the vapour-proof seal provides less than 6% evaporation of fluid inside the storage well, preferably less than 4%. Further, as the content of the storage well can be sealed for a long period of time, assay developers have more degrees of freedom to operate to, resulting in faster and more efficient assays. For example, the cap can be used in conjunction with a biochip storage well to eliminate the loss of fluid form the biochip storage well during a 60 minute 60° C. incubation.

In a preferred embodiment, the material composition of the cap has thermal properties compatible with temperature set-points and ramp rates associated with PCR (Polymerase Chain Reaction) and can be exposed to typical thermal cycling conditions indefinitely without suffering physical deterioration or physical changes in dimensions that could compromise a vapour proof seal between the cap and an interfacing fluid container. The materials are also preferably resistant and unreactive to the environments presented (e.g. in terms of chemistry, toxicology, pH etc.) by the chemical types during PCR.

In a preferred embodiment, an automated pipette can be controlled to aspirate and dispense the required fluid into the biochip storage well, then to pick up and place the cap accurately. The biochip storage well can then be clamped by another robotics system, which applies pressure to the cap, during the incubation. After unclamping, the automated pipette is free to remove the well and continue the assay without loss of fluid or contamination.

In a preferred embodiment, the cap according to the present invention includes a component extending away from the resilient sealant layer to allow the cap to be manipulated. Preferably this component extending away from the resilient sealant layer is cylindrical. In a preferred embodiment, the cylindrical component is a hollow tube through which a pipette can be inserted. This component allows the cap to be picked up and placed down accurately by a manual pipette or a simple robotics assembly. In a preferred embodiment, the cap can also be moved through simple automation, without the requirement for complicated robotics. The seal between the biochip storage well and the cap does not use a screw or plug, rather the cap rests on top of the receptacle and a small force is applied downward. As such, when the force is removed, the cap is free to lift off or slide off easily.

In one embodiment of the present invention, the hollow tube of the component extending away from the resilient sealant layer comprises a pierceable membrane at the base of the tube. This allows for a pipette tip to access the biochip storage well without removing the cap. Preferably, the membrane is frangible, allowing a pipette tip to pierce the membrane multiple times without the risk of contaminating the environment or the sample.

In a preferred embodiment, certain parts of the cap are made from plastic. More specifically, the flat top section and the cylindrical component are plastic. The cap can be integrally formed or adhered. The design of the plastic part of the cap is suitable for injection moulding (PP) and mass manufacture. The resilient sealant layer can be easily cut using a die cutter and is suitable for a manufacturing line. The resilient sealant layer and the plastic cap part are preferably bonded by an adhesive.

In a second embodiment of the present invention, the cap comprises two opposing slide members, each defining a groove to enable the cap to slide onto a corresponding flange extending along the perimeter of the biochip storage well and thereby forming the vapour-proof seal with the line contact interface formation extending around the perimeter of the biochip storage well. The slide members and flange are constructed so that once the cap has been slid onto the well, an interference fit is achieved between the resilient layer and the line contact interface formation thereby providing the pressure needed to achieve the vapour-proof seal. The resilient layer is as described herein, and is preferably polytetrafluoroethylene (PTFE), polychlorotrifluoroethylene (PCTFE) or polyethylene (PE).

In this second embodiment, the biochip storage well and the cap can optionally be attached to a support member. The support member comprises a recess in which the biochip storage well sits, and the corresponding flange extending along the perimeter of the biochip storage well is formed by the support member. Thus the cap according to the second embodiment can slide onto the biochip storage well or the support member in which the biochip storage well sits. The support member may comprise a raised component which prevents the cap from sliding beyond a desired point by engaging with a leading end of the cap.

The cap can preferably slide along a single plane in two directions, corresponding to on and off the biochip storage well. Preferably, the cap comprises a component extending away from the resilient sealant layer which facilitates the sliding motion of the cap. This can be by interface with an automatic actuator.

The cap according to the second embodiment of the present invention can include any of the preferred features described herein.

The cap of this embodiment preferably has less than 1% water absorption, low thermal conductivity and a melting temperature over 150° C. The dimensions of the cap are typically 13×13×7 mm, however, any other suitable dimensions may be used.

The cap may slide onto the biochip storage well or support member comprising the biochip storage well. The cap of the second embodiment imparts a force of typically 10-50 N, preferably 10-30 N, most preferably 15 N onto the line contact interface of the biochip storage well, thereby forming a vapour-proof seal. When the cap covers the biochip well, the vapour proof seal provides less than 5% evaporation of the fluid within.

The present invention defines an assay assembly device comprising the cap of the second embodiment, the biochip storage well and, optionally, the support member.

The present invention also defines a method of sealing a biochip storage well having a line contact interface surrounding the perimeter thereof, with a cap according to the second embodiment, comprising the steps of;
  providing a biochip storage having a corresponding flange extending along the perimeter of the biochip storage well;
  optionally providing an support member having a recess in which the biochip storage well sits, wherein the corresponding flange extending along the perimeter of the biochip storage well is formed by the support member;
  applying pressure such that the cap slides onto the corresponding flange extending along the perimeter of the biochip storage well and forms a vapour-proof seal with the line contact interface of the biochip storage well.

In this method, pressure is applied in order to slide the cap into a closed position. Once the cap is in a closed position, and covers the biochip storage well, the interference fit between the line contact interface formation and the cap imparts a force of typically 10-50 N, preferably 10-30 N, most preferably 15 N onto the line contact interface, thereby forming a vapour-proof seal. The sliding motion can be achieved by using a simple robotics system, which interacts with the component extending away from the resilient layer in order to manipulate the cap. An assay can then be performed, for example at 60° C. for 60 minutes, to the sealed storage well. After this time, pressure can be applied to slide the cap into an open position, thus releasing the vapour-proof seal. Again, this can be achieved by using a simple robotics system.

Preferred embodiments of the invention will now be explained with reference to the accompanying drawings, in which.

Figure 1A:
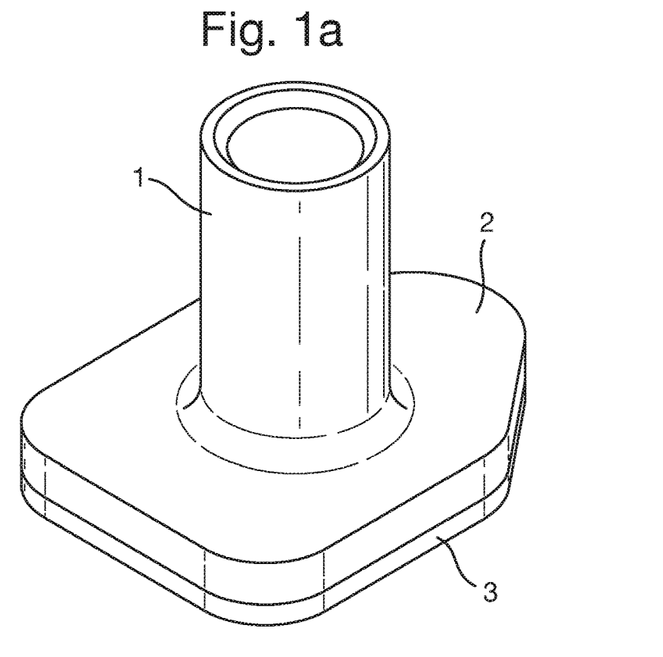
FIGS. 1a and 1b are perspective views of a first embodiment of a biochip well cap according to the invention.
Figure 1B:
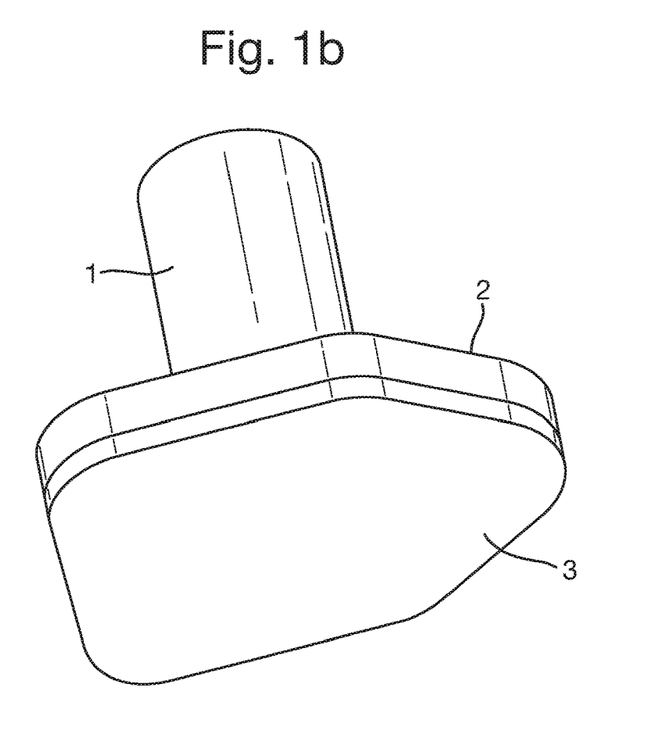

FIGS. 1a and 1b illustrate a preferred embodiment of the cap according to the present invention, comprising a flat top section 2 and a resilient sealant layer 3.

The flat top section 2 is made of a plastic material and is bonded to the resilient sealant layer 3 by adhesive. Optionally, a component 1 extending away from the resilient sealant layer is present. This component 1 is cylindrical in shape. Component 1 is in the shape of a hollow tube, and is made of a plastic material and could be integrally formed by injection moulding, with the flat top section 2. The hollow tube of component 1 may contain a pierceable membrane at its base aligning with a hole in the flat top section 2 and the resilient sealant layer 3 (not shown).

The cylindrical component 1 is typically 12 mm in height and is hollow with an internal diameter of 5 mm, and is joined to the flat top section 2. The flat top section 2 covers an area of 225 mm$^2$ and is composed of a square area with an adjoining triangular area, with all corners rounded to 3 mm radii, and is preferably 2 mm thick. The sealant layer 3 covers the same area and dimension as the flat top section 2 and is preferably 1 mm thick.

Figure 2:
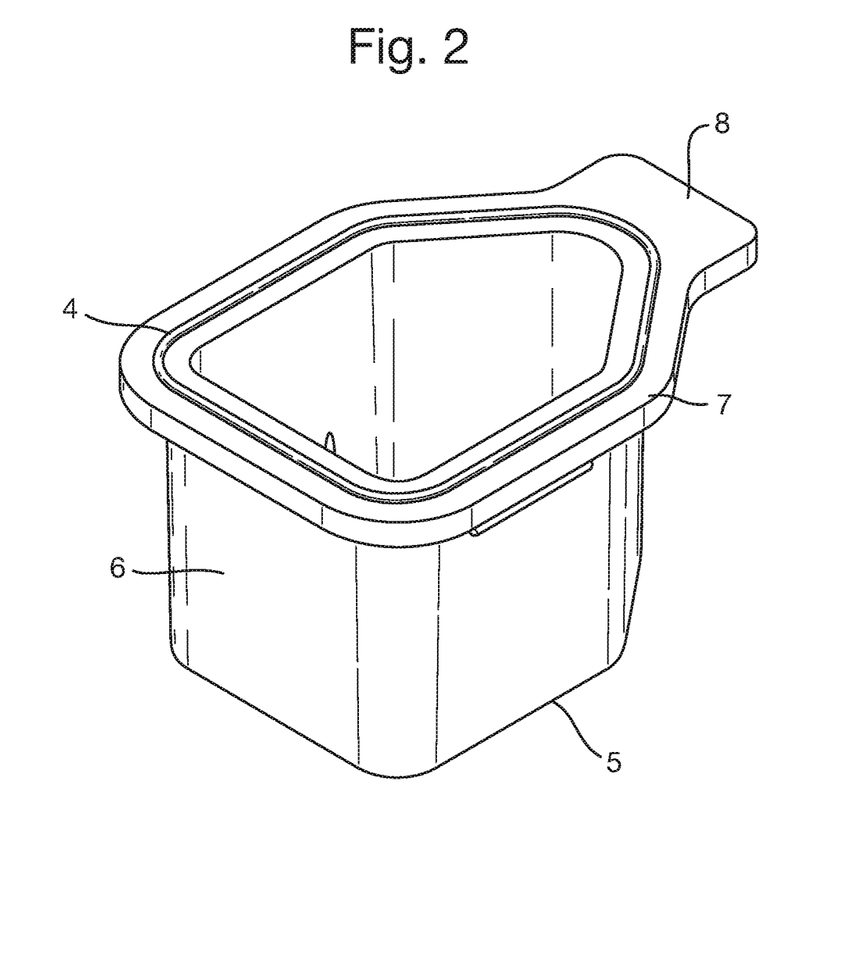
FIG. 2 is a perspective view of biochip storage well to be used in conjunction with the biochip well cap.

FIG. 2 illustrates a biochip storage well or receptacle which can be used to form a vapour-proof seal with the cap as shown in FIGS. 1a and 1b. The biochip storage well has a base 5 and side wall 6, and is adapted to receive a biochip (not shown). A rimmed section 7 is formed on top of the side wall 6. The rimmed section 7 projects laterally outwards from the side wall 6 in the form of a flange, and includes a tab 8, allowing the storage well to be handled. Most importantly, the biochip storage well has a line contact interface in the form of a knife-edge formation 4 which projects from, extends around the perimeter of and is integrally formed with the rimmed section 7. The cap of FIGS. 1a and 1b extends across the entire biochip storage well of FIG. 2, forming under pressure a tight vapour-proof seal between the resilient layer 3 and the knife-edge interface 4 and thus closing the storage well.

Figure 3:
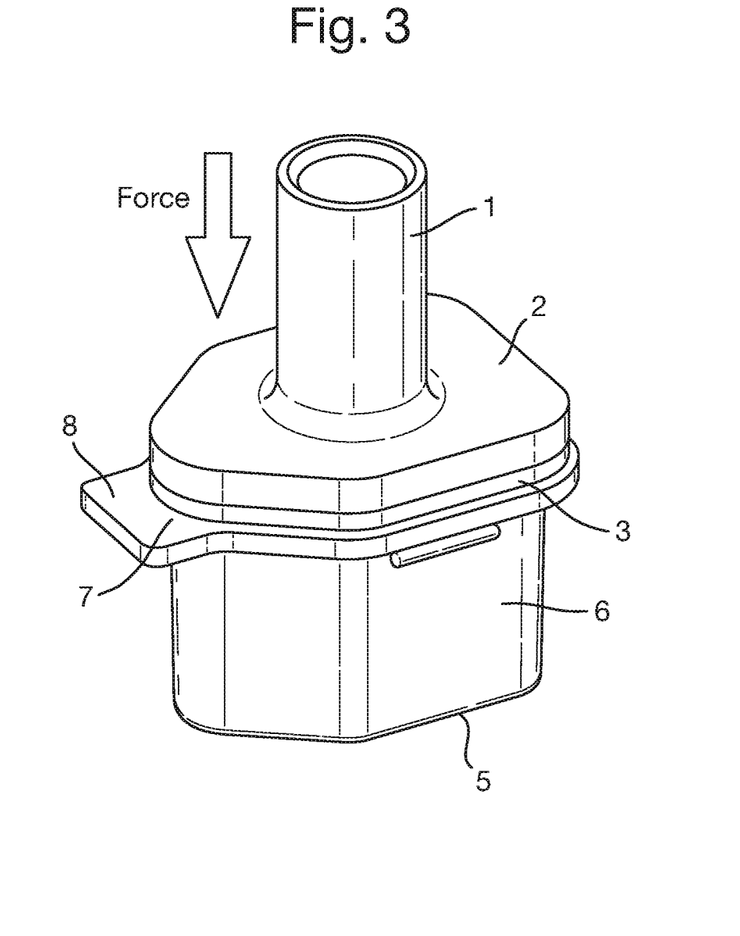
FIG. 3 illustrates a method of sealing the biochip storage well with the biochip well cap

FIG. 3 illustrates the method of sealing the biochip storage well shown in FIG. 2, with the cap shown in FIGS. 1a and 1b. The flat top section of the cap 2, bonded to the resilient sealant layer 3 is the same shape as the top face of the biochip storage well. The resilient sealant layer 3 is placed onto the knife-edge interface 4, extending around the perimeter of the rimmed section 7. Force typically of 10-50 N, preferably 10-30 N, most preferably 15 N is applied on the top flat section 2 of the cap, pressing the raised knife-edge interface 4 into the resilient sealant layer 3, forming a vapour-proof seal. In use, the biochip storage well cap is placed onto the biochip storage well. This can be achieved using a simple robotics system or a manual pipette (not shown). For example, a robotic arm can grasp the cylindrical component 1 of the cap in order to move the cap onto the biochip storage well, so that the resilient sealant layer 3 covers the knife-edge 4. The robotic arm can then push down onto the flat section 2 of the cap, applying the required force to achieve sealing. A pipette can be inserted, either manually or robotically, into the hollow tube 1 to pierce the pierceable membrane aligning with a hole in the flat top section 2 and the resilient sealant layer 3. The pipette can dispense or aspirate fluid into the sealed biochip storage well, which is under sustained pressure. An assay can then be performed, for example at 60° C. for 60 minutes, to the sealed storage well. After this time, the seal is released and the cap is removed, by the simple robotics system.

Figure 6:
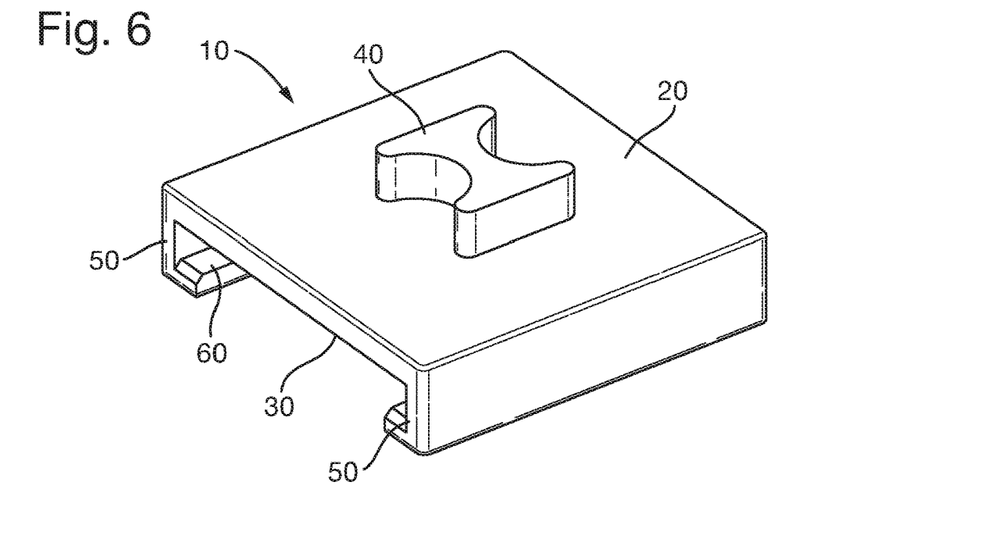
FIG. 6 illustrates a biochip well cap according to the second embodiment of the present invention.
Figure 7:
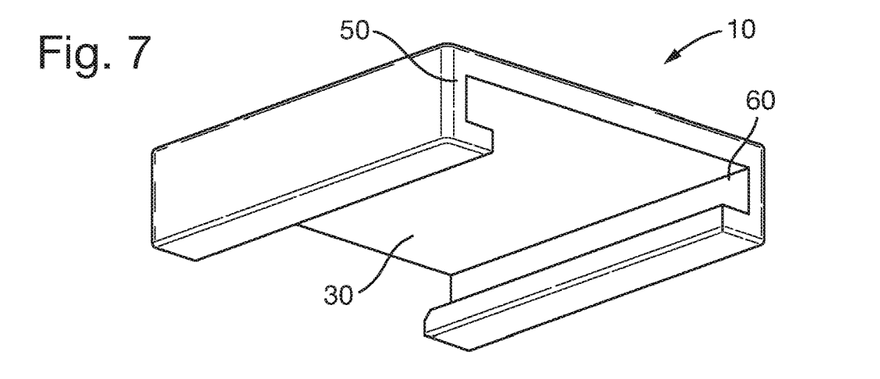
FIG. 7 illustrates a biochip well cap according to the second embodiment of the present invention viewed from below.

FIG. 6 illustrates the biochip well cap of the second embodiment 10. It comprises a flat top section 20 and a resilient sealant layer 30. Preferably the flat top section 20 and resilient sealant layer 30 are integrally formed, however they can form separate layers. Preferably the flat top section 20 and resilient sealant layer 30 are made of polytetrafluoroethylene (PTFE), polychlorotrifluoroethylene (PCTFE) or polyethylene (PE). A component 40 extending away from the resilient sealant layer is present and allows the cap to be manipulated. The cap comprises two opposing slide members 50, each defining a groove 60, to enable the cap 10 to slide onto a corresponding flange extending along the perimeter of the biochip storage well. FIG. 7 illustrates the cap of the second embodiment when viewed from below.

Figure 8:
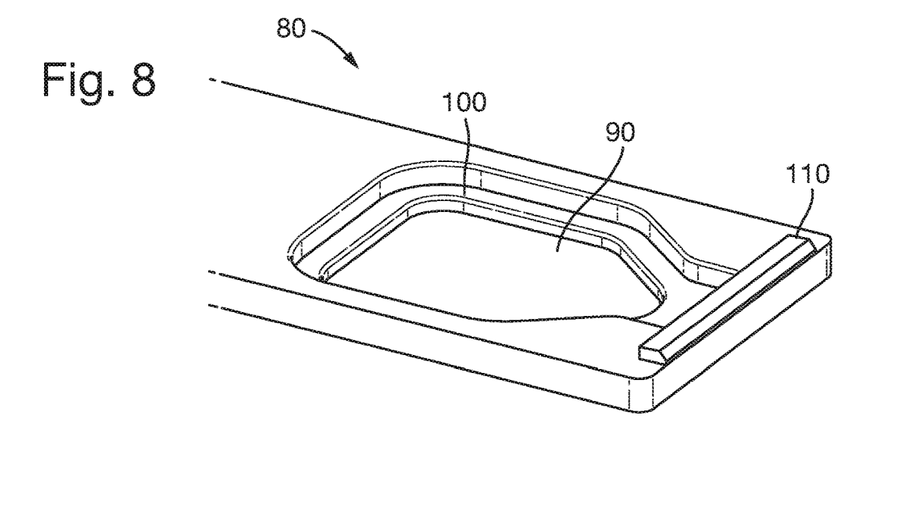
FIG. 8 illustrates a support member.

FIG. 8 illustrates an elongate support member 80, which can be used in the assay assembly of the present invention. The support member 80 comprises a recess 90 in which the biochip storage well sits. A cut away section 100 extends around the perimeter of the recess 90. The support member also comprises a raised member 110, which prevents the cap from sliding beyond a desired point.

Figure 9:
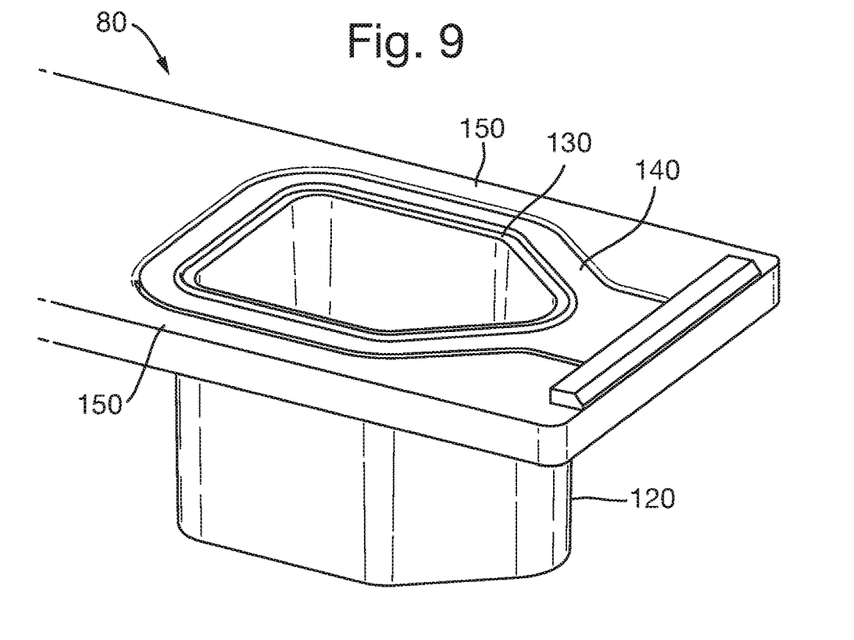
FIG. 9 illustrates a biochip storage well and a support member.

FIG. 9 illustrates the biochip well 120 sitting in the recess of the support member 80. The biochip storage well 120 comprises a knife-edge interface 130 extending around the perimeter of the biochip storage well 120. The biochip storage well 120 is supported in the support member 80 as the rimmed section 140 sits in the cut away section 100 of the support member 80. In this embodiment, the corresponding flange extending along the perimeter of the biochip well is formed by the edges 150 of the support member.

Figure 10:
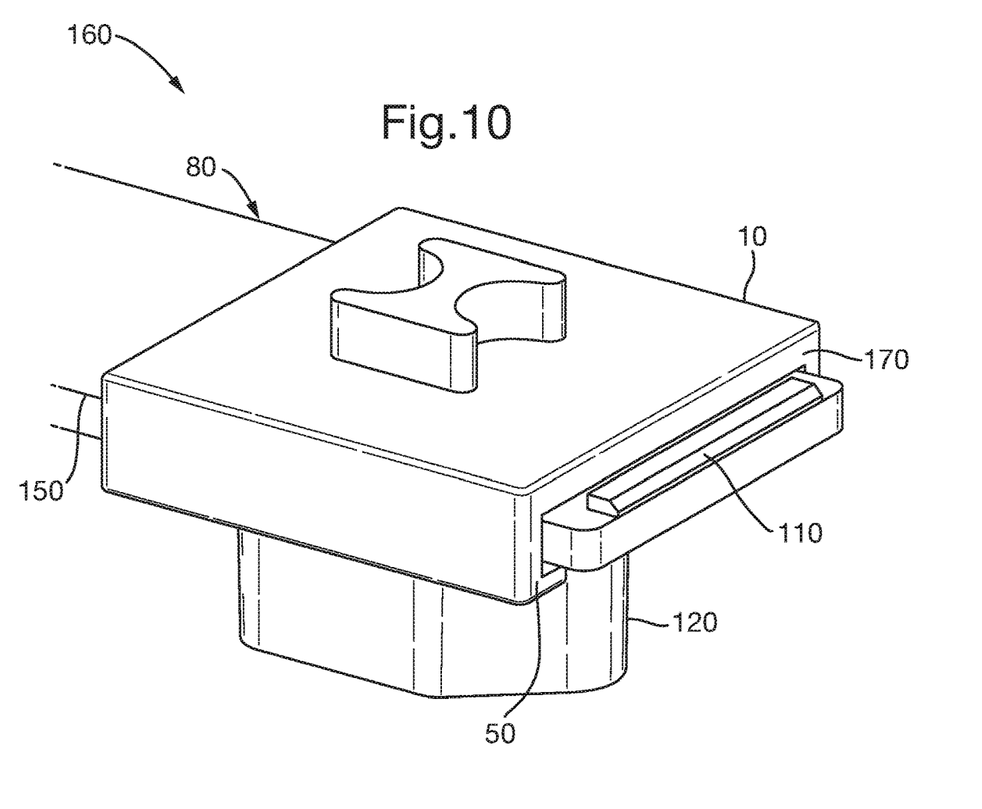
FIG. 10 illustrates an assay assembly device comprising the cap of the second embodiment, biochip storage well and a support member.

FIG. 10 illustrates the assay assembly device 160 comprising the cap of the second embodiment 10, the biochip storage well 120 and the support member 80. The biochip storage well 120 sits in the recess 90 of the support member 80 as shown in FIG. 9. The cap 10 slides along the edges 150 of the support member until the leading end of the cap 170 engages the raised member 110 which prevents the cap 10 sliding further. The slide members 50 are a tight fit on the support member 80 so that the resilient sealant layer 30 is forced under pressure onto the knife-edge interface 130. The resilient layer 30 of the cap 10 thus forms a vapour-proof seal with the knife-edge interface 130 extending along the perimeter of the biochip storage well 120. In this case no extra pressure is required to achieve the seal.

EXAMPLES

The invention will now be described in relation to the following non-limiting examples. The amount of evaporation occurring in an assay assembly comprising a cap according to the first embodiment of the present invention and biochip storage well as illustrated in FIG. 2 was determined, in order to investigate the vapour-proof seal between the resilient sealant layer and knife-edge interface. A force of 50 N was applied to the cap to act as the clamping force.

Figure 4:
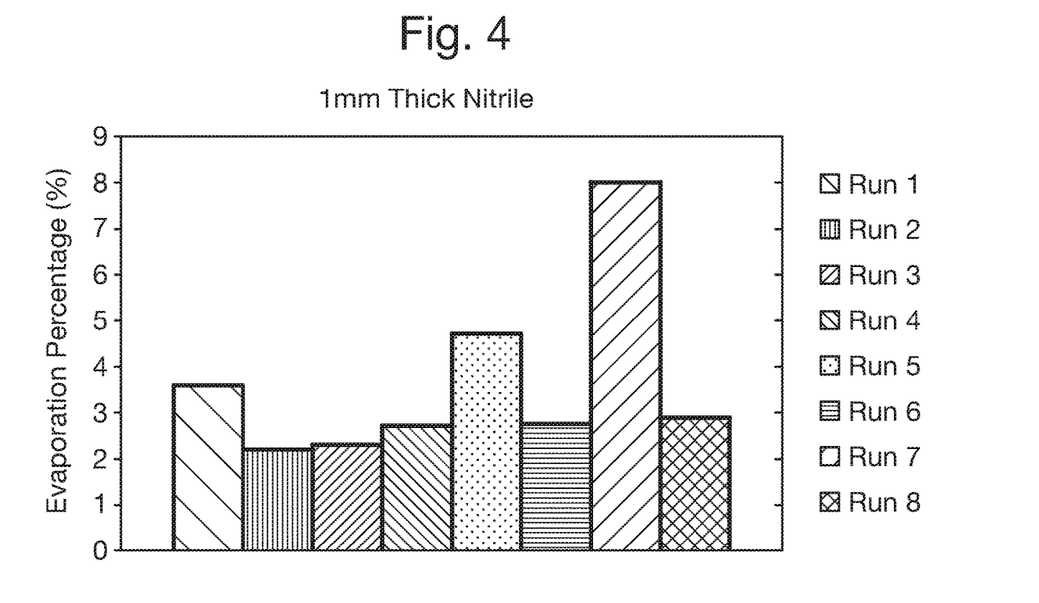
FIG. 4 is a graph showing the percentage evaporation of liquid for assay assemblies according to the invention, when the resilient sealant layer is 1 mm thick nitrile

The test method used to determine the % of evaporation was as follows;
Heat wells to 60° C. for 1 hour
Place 550 μl of deionised water into the wells
Weigh the wells before and after test
Well caps should be clamped at 50 N Table 1 shows the results for the above method when testing a nitrile sealant layer of 1 mm. The cap according to the present invention, comprising a 1 mm nitrile sealant layer was placed onto the storage well of FIG. 2 containing 550 μl of deionised water. A force of 50 N was applied, and the assembly heated to 60° C. for 1 hour. The weight of the sample and storage well/cap was measured at various stages, as shown in Table 1 below. The percentage difference was calculated using the results from the test. The difference in weight of the wells before and after the test was attributed to a small amount of vapour condensing on the surface of the cap exposed to the vapour during the test. A small degree of experimental error is also expected. FIG. 4 shows the results in bar chart form.

TABLE 1

| Run | Weight without Sample before test (g) | Weight of well with sample before test (g) | Weight of Sample prior (g) | Weight of well after test (g) | Weight of sample after test (g) | Difference Percentage (%) |
| --- | --- | --- | --- | --- | --- | --- |
| 1 | 2.7735 | 3.3219 | 0.5483 | 3.3021 | 0.5286 | 3.59 |
| 2 | 2.6696 | 3.2700 | 0.6004 | 3.2568 | 0.5872 | 2.20 |
| 3 | 2.7569 | 3.3267 | 0.5698 | 3.3119 | 0.5550 | 2.59 |
| 4 | 2.6716 | 3.1275 | 0.4559 | 3.1151 | 0.4435 | 2.72 |
| 5 | 2.7255 | 3.2823 | 0.5568 | 3.2561 | 0.5306 | 4.71 |
| 6 | 2.7589 | 3.3127 | 0.5538 | 3.2975 | 0.5386 | 2.75 |
| 7 | 2.7849 | 3.4232 | 0.6383 | 3.3719 | 0.5870 | 8.01 |
| 8 | 2.8199 | 3.3003 | 0.4804 | 3.2864 | 0.4665 | 2.89 |

Figure 5:
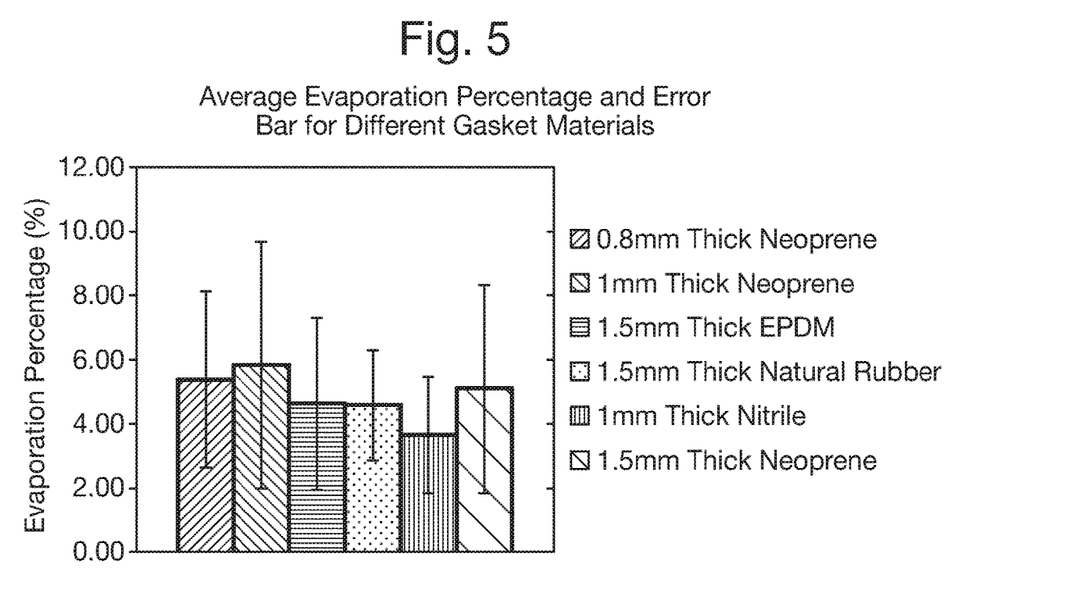
FIG. 5 is a graph showing the average percentage evaporation of liquid per resilient sealant layer tested.

The test method as described above was then repeated for various different polymer sealants, specifically, 0.8 mm thick neoprene, 1 mm thick neoprene, 1.5 mm thick EPDM, 1.5 mm thick natural rubber and 1 mm thick nitrile. FIG. 5 shows the average percentage evaporation for each sealant.

CONCLUSION

Analysis of FIG. 5, a graph displaying the average evaporation percentages for the different gasket materials upon which the evaporation tests were completed, clearly shows that 1 mm thick Nitrile has performed the best compared to the other materials.

The invention claimed is:

1. An assay assembly comprising a biochip storage well having a base and one or more side walls, adapted to receive a biochip, with a line contact interface formation in the form of a knife-edge facing away from the base and extending along an upwardly facing perimeter of the one or more side walls and a cap comprising a resilient sealant layer, and comprising two opposing slide members, each defining a groove to enable the cap to slide onto a corresponding flange extending along the perimeter of the biochip storage well and thereby forming a vapour-proof seal with the line contact interface formation extending around the perimeter of the biochip storage well when the resilient sealant layer of the cap is applied, with a pressure, against the line contact interface formation and comprising a support member having a recess in which the biochip well sits, wherein the corresponding flange extending along the perimeter of the biochip storage well is formed by the support member.

2. The assay assembly according to claim 1, wherein the pressure applied is in the range of 10-50 N.

3. The assay assembly according to claim 1, wherein the cap further includes a component extending away from the sealant layer to allow the cap to be manipulated.

4. The assay assembly according to claim 3, wherein the component extending away from the sealant layer is a hollow tube through which a pipette can be inserted.

5. The assay assembly according to claim 4, further comprising a pierceable membrane at the base of the hollow tube.

6. The assay assembly according to claim 1, wherein the resilient sealant layer is a polymer sealant.

7. The assay assembly according to claim 6 wherein the resilient sealant layer is polytetrafluoroethylene (PTFE), polychlorotrifluoroethylene (PCTFE) or polyethylene (PE).

8. The assay assembly according to claim 6, wherein the resilient sealant layer is a nitrile layer.

9. The assay assembly according to claim 8, wherein the nitrile sealant layer is 0.1 to 10 mm in thickness.

10. The assay assembly according to claim 1, further comprising a hydrophobic layer, coated onto the resilient sealant layer.

11. The assay assembly according to claim 1, wherein the cap is made from injection moulding.

12. The assay assembly according to claim 1, wherein the cap comprises a plastic flat top section.

13. A method of sealing the assay assembly of claim 1, comprising the steps of:
   placing the cap onto the biochip storage well wall so that the resilient sealant layer is above the line contact interface formation;
   applying external force onto the cap so that the cap closes the biochip storage well and the resilient sealant layer is pressed into the line contact interface formation, forming a vapour-proof seal, wherein the biochip storage well has a corresponding flange extending along the perimeter of the biochip storage well and wherein the cap slides onto the corresponding flange extending along the perimeter of the biochip storage well so as to form a vapour-proof seal with the line contact interface formation of the biochip storage well.

14. The method according to claim 13 wherein the pressure applied is in the range of 10-50 N.

15. The method according to claim 13, wherein the vapour-proof seal provides less than 6% evaporation of the fluid within.

16. The method according to claim 13, wherein the line contact interface formation is in the form of a knife-edge.

* * * * *